United States Patent [19]
Saito et al.

[11] Patent Number: 5,180,487
[45] Date of Patent: Jan. 19, 1993

[54] PUMP APPARATUS FOR TRANSFERRING A LIQUIFIED GAS USED IN A RECYCLE CHROMATOGRAPH

[75] Inventors: Muneo Saito, Hachioji; Yoshio Yamauchi, Hini, both of Japan

[73] Assignee: Nihon Bunko Kogyo Kabushiki Kaisha, Tokyo, Japan

[21] Appl. No.: 715,880

[22] Filed: Jun. 17, 1991

Related U.S. Application Data

[60] Division of Ser. No. 471,021, Jan. 25, 1990, abandoned, which is a continuation of Ser. No. 249,003, Sep. 23, 1988, abandoned.

[30] Foreign Application Priority Data

Sep. 25, 1987 [JP] Japan ................. 62-240360

[51] Int. Cl.$^5$ ............................................. B01D 15/08
[52] U.S. Cl. ............................ 210/198.2; 210/656; 210/659; 210/101; 210/137
[58] Field of Search ............... 210/659, 101, 137, 143, 210/198.2, 656; 55/386

[56] References Cited

U.S. PATENT DOCUMENTS

| | | | |
|---|---|---|---|
| 3,398,689 | 8/1968 | Allington | 210/101 |
| 3,443,691 | 5/1969 | Nilsson | 210/101 |
| 3,686,117 | 8/1972 | Lauer | 210/659 |
| 4,137,161 | 1/1979 | Shimada | 210/659 |
| 4,239,623 | 12/1980 | Schrenker | 210/198.2 |
| 4,271,697 | 6/1981 | Mowery | 210/659 |
| 4,311,586 | 1/1982 | Baldwin | 210/101 |
| 4,388,184 | 6/1983 | Brow | 210/101 |
| 4,403,866 | 9/1983 | Falcoff | 366/132 |
| 4,478,720 | 10/1984 | Perrut | 210/198.2 |

FOREIGN PATENT DOCUMENTS

| | | | |
|---|---|---|---|
| 2759933 | 7/1988 | European Pat. Off. | 210/198.2 |
| 2036525 | 6/1974 | Fed. Rep. of Germany | 210/656 |
| 2729317 | 11/1977 | Fed. Rep. of Germany | 210/101 |
| 2729462 | 1/1979 | Fed. Rep. of Germany | 210/198.2 |
| 2527934 | 6/1982 | France | 210/659 |

OTHER PUBLICATIONS

Snyder, Introduction to Modern Liquid Chromatography, John Wiley & Sons, Inc., New York pp. 519-522 & 98-99.

*Primary Examiner*—Ernest G. Therkorn
*Attorney, Agent, or Firm*—Browdy and Neimark

[57] ABSTRACT

It is an object to provide a recycle chromatograph with supercritical fluid mobile phase for separating a sample into components by recycling a mobile phase which includes modifier solvent for the purpose of taking a desired component.

It is structured in such a manner that a recycling pump (10), a column (14), a detector (16), and a three-way valve (18) are connected in a sequential order as described above to form a closed loop which acts as a recycle flow line. A back-pressure regulator (20) is connected to the remainder port (C) of this three-way valve (18), and a mobile phase supplying and pressurizing device (30, 38, 30A, 48) for supplying the mobile phase under a predetermined pressure is connected to a flow line between the three-way valve (18) and the recycling pump (10).

By means of this mobile phase supplying and pressurizing device and the recycle closed loop, (the column pressure drop $\Delta p$)/(column plate number) can be reduced, whereupon the column effective plate number can be increased. Thus, a sufficient resolution rate for fractionating a component can be obtained after appropriate recycling times.

Furthermore, by combining the mobile phase supplying device (30, 38 30A, 38A, 48) and the back-pressure regulator (20), the internal pressures in the column and the detector can be kept above the critical pressure even if unnecessary components are being removed or a necessary component is being fractionated. As a result of which fractionation can be performed.

4 Claims, 5 Drawing Sheets

PUMP APPARATUS FOR TRANSFERRING A LIQUIFIED GAS USED IN A RECYCLE CHROMATOGRAPH

This application is a divisional application of application Ser. No. 07/471,021, filed Jan. 25, 1990 itself a continuation application of application Ser. No. 07/249,003, filed Sep. 23, 1988, now abandoned.

BACKGROUND OF THE INVENTION

1. Field of the Invention

This invention relates to a recycle chromatograph with supercritical fluid which separates a mixture into components by recycling a mobile phase through a separation column repeatedly until the mixture is separated sufficiently, whereby a desired component can be fractionated.

2. Description of the Prior Art

Carbon dioxide is the substance most widely used as the mobile phase in supercritical fluid chromatography. Although carbon dioxide exhibits solubility when it is a liquefied gas or a supercritical fluid, i.e., its density is liquid like density 0.3 to 1.2 g/ml, the solubility thereof with respect to the solute becomes substantially zero when the pressure is reduced to atmospheric pressure, whereupon it becomes a normal gas. Therefore, the solute of a sample can be easily separated from the fluid with high purity when carbon dioxide is used as the mobile phase in supercritical fluid chromatography.

However, many conventional supercritical fluid chromatographs are designed to use only as an analyzing device, but not as a fractionating device, that is, a device for separating and purifying the desired component contained in a sample mixture. The major reason for this lies in that when fractionation is intended, a proper column separation efficiency needs to be realized by using a relatively long column with large diameter for high sample loading capacity, resulting in high mobile phase flowrates.

In order to overcome the above-described problem, a recycle method is widely used in liquid chromatography. This recycle method is a method in which the column's effective length is increased by repeatedly-passing the mobile phase containing solute through the column via the mobile phase delivery pump, the separation or elution takes place without any solvent consumption, and a portion of column effluent containing a desired component can be drawn out for fractionation in which period the same amount of solvent can be fed. If this recycle method can be applied to a recycle chromatograph with a supercritical fluid as the mobile phase, its applicable range can be widened.

It is well known that, in SFC, a high pressure drop causes density decrease along the column toward outlet, resulting in reducing the efficiency. Therefore, the obtainable plate number is not in proportion to the column length.

In this regard, the recycle operation of SFC is very favorable, because the column efficiency is increased by a factor of the number of recycles without increasing the back-pressure, if extracolumn band broadening is negligible.

SUMMARY OF THE INVENTION

In view of these problems, it is an object of the present invention to provide a recycle chromatograph which uses supercritical fluid as its mobile phase.

To this end, the present invention provides a recycle chromatograph with supercritical fluid as mobile phase comprising: a recycling pump for transferring a mobile phase at a predetermined flowrate; a sample injector the inlet of which is connected to the outlet of the recycling pump via a flow line; a first column the inlet of which is connected to the outlet of the sample injector via a flow line, said first column being filled with a stationary phase; a detector the inlet of which is connected to the outlet of the first column via a flow line, said detector detecting the components of a sample; means for switching a flow line the inlet of which is connected to the outlet of the detector, while either of the two outlets of which is connected to the recycling pump via a flow line, the two outlets being selectively connected to the inlet thereof; a first back-pressure regulator or a resistance pipe the inlet of which is connected to another outlet of the flow line switching means via a flow line, while the outlet of said first back-pressure regulator a resistance pipe is connected to the atmosphere; and a pressurizing means which is connected to a flow line between either of the two outlets of the flow line switching means and the inlet of the recycling pump via a flow line, said mobile phase supplying means supplying the mobile phase under a predetermined pressure to the recycling pump.

By this recycle chromatograph, (the column pressure drop $\Delta p$)/(column plate number) can be reduced, whereupon the effective column plate number can be increased. Thus, a sufficient resolution for fractionating a component can be obtained after appropriate recycling times. Furthermore, by combining this means for supplying and pressurizing a mobile phase and the back pressure regulator or a resistance pipe, the internal pressure of the column and the detector can be maintained above a critical pressure even while unnecessary components are removed or a necessary component is fractionated. As a result of this, fractionation can be performed.

The mobile phase supplying means, for example, comprises: a first pump for transferring a liquefied gas at a predetermined flowrate; a second back-pressure regulator which is connected to the outlet flow line of the first pump via a flow line, said second back-pressure regulator maintaining the back pressure at a predetermined level; and a second pump the outlet of which is connected to a flow line between an intersecting point connecting the outlet flow line of the first pump and the inlet flow line of the second back-pressure regulator and the outlet of the first pump or the inlet flow line of the first pump via a flow line, said second pump transferring modifier solvent at a predetermined flowrate.

According to the above-described structure, the supply pressure can be maintained at a predetermined level and the mixture ratio between the liquefied gas and the modifier solvent can be maintained at the predetermined ratio between the predetermined flowrate of the first pump and that of the second pump even if the supplied flow is a very small amount of several $\mu l/min$ or less or even if this supplying flow rate is varied. As a result of this, the reproducibility of the peak retention times is improved and the base line of the output from the detector can be stabilized.

DESCRIPTION OF THE PREFERRED EMBODIMENT

Embodiments of the present invention will be described below with reference to the accompanying drawings.

(1) First embodiment

Figure 1:
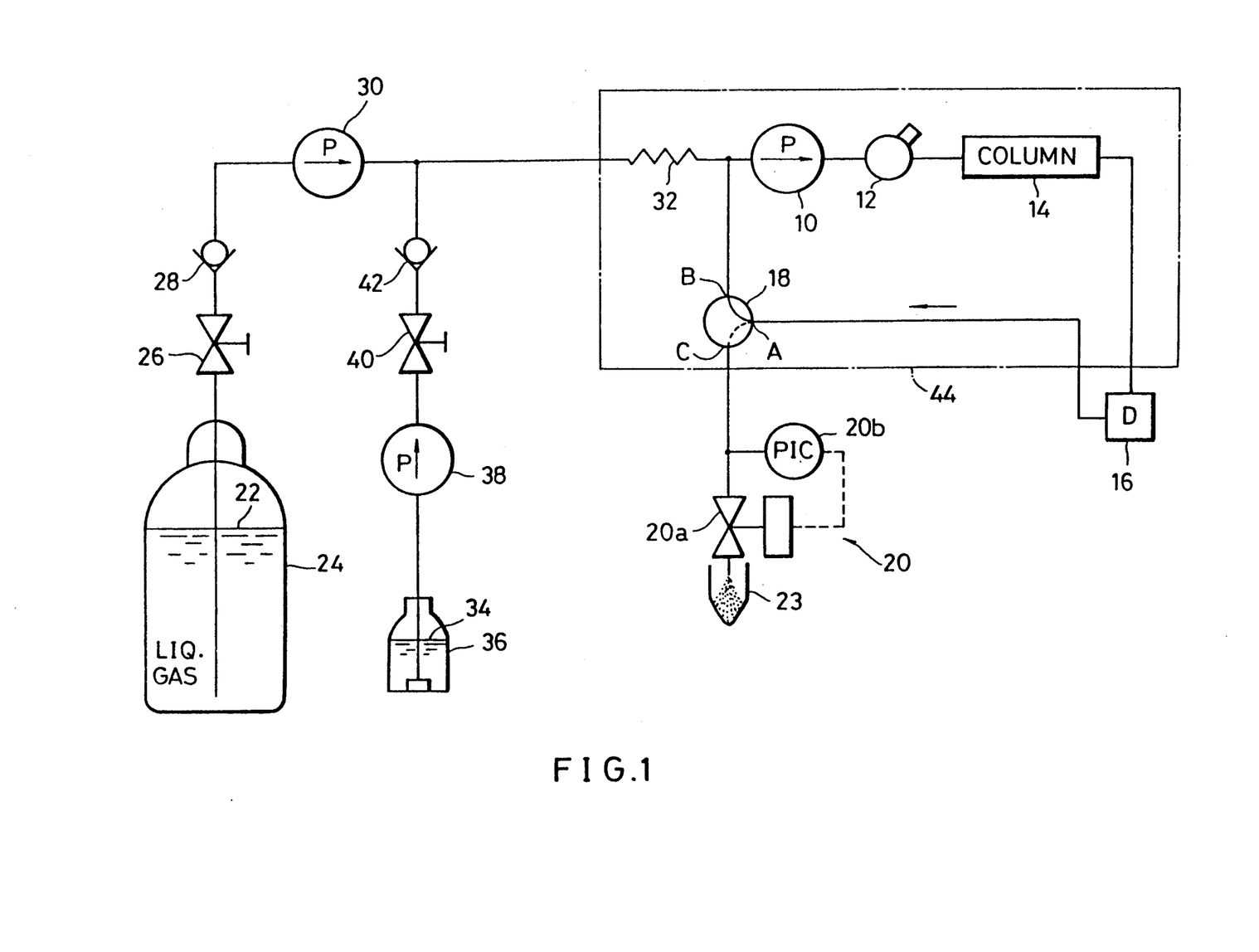
FIG. 1 shows the flow line of a recycle chromatograph with supercritical fluid according to a first embodiment of the present invention.

FIG. 1 shows a recycle chromatograph with supercritical fluid (Recycle SFC) according to a first embodiment. This recycle SFC comprises a recycle portion, a fractionating portion, and a mobile phase supplying portion.

The recycle portion comprises the following components connected in the sequential order as described hereinafter via piping: a recycling pump 10 for transferring a predetermined flow; a sample injector 12; a column 14 filled with a solid phase; a detector 16 such as a UV detector which can detect a sample component under a high pressure; and a three-way valve 18. As a result of this, a closed loop serving as a recycle flow line is formed. The three-way valve 18 is so arranged that a port A thereof is connected to the outlet of the detector 16, while a port B thereof is connected to the inlet of the recycling pump 10. The port A is selectively connected to either the port B or C.

The fractionating portion comprises: a back-pressure regulator 20 whose inlet is connected to the port C of the three-way valve 18 while its outlet is connected to atmosphere; and a container 23 for accumulating the fractionated component. The back pressure regulator 20 comprises: a pressure regulating valve 20a; and a pressure indicating regulator 20b which detects and indicates the pressure of the upper stream to the pressure regulating valve 20a and controls the pressure regulating valve 20a for the purpose of maintaining the detected pressure at a predetermined level which exceeds a critical pressure. This pressure regulating valve 20a is a valve having a relatively small capacity (for example 10 μl), and offering an excellent recovery efficiency, for example, a valve spindle vibrating solenoid valve whose valve spindle moves in the axial direction thereof for the purpose of closing the flow line when the pressure is below a predetermined pressure, while opening the same when the pressure exceeds a predetermined pressure. This valve spindle vibrating solenoid valve was disclosed by an inventor of the present invention in U.S. patent application Ser. No. 07/143,928 or Europe Patent Application Laid-Open No. 0 275 933.

The mobile phase supplying portion in principle comprises the following components that are connected to each other in a series via piping in the sequential order as described hereinafter: a cylinder 24 wherein a liquefied gas 22 which serves as the mobile phase is enclosed; a shut-off valve 26; a check valve 28 for preventing reverse flow to the shut-off valve 26 which causes a pressure reduction; a pressurizing pump 30 for transferring the liquefied gas 22 for the purpose of raising the outlet pressure up to a predetermined critical pressure; and a preheating coil 32. The outlet of the preheating coil 32 is connected to the inlet of the recycling pump 10. The function performed by this check valve 28 can be as well performed by the shut-off valve 26. The shut-off valve 26 is usually provided for the cylinder 24.

In order to elute polar compounds with non-polar fluid such as carbon dioxide as the mobile phase, a polar solvent such as alcohol needs to be mixed as a modifier solvent with the mobile phase. In order to obtain reproducible peak retention times, the ratio of mixture of the above two components needs to be kept constant.

Therefore, the following components are connected to each other via piping in a series in the sequential order as described hereinafter: a reservoir 36 which contains a modifier solvent 34; a fluid delivery pump 38 for transferring the modifier solvent 34 in a quantity in proportion to the delivery of the pressurizing pump 30; a shut-off valve 40; and a check valve 42 for preventing reverse flow to the shut-off valve 40 which causes a pressure reduction. The outlet of the check valve 42 is connected to the piping between the pressurizing pump 30 and the preheating coil 32 via piping. It may be arranged in such a manner that either the shut-off valve 40 or the check valve 42 is provided.

In order to maintain the mobile phase as a supercritical fluid, the above-described recycling pump 10, the sample injector 12, the column 14, the three-way valve 18 and the preheating coil 32 are accommodated in an oven 44 which maintains its predetermined internal temperature which exceeds a critical temperature.

An operation of the thus-structured first embodiment in case where only the liquefied gas 22 is used as the mobile phase will be described.

First, the temperature of the inside of the oven 44 is raised to a predetermined temperature which exceeds the critical temperature. The pressure of the pressure regulator 20b is set to the desired predetermined level which exceeds the critical pressure. Next, the flow line in the three-way valve 18 between the ports A and C is opened, the shut-off valve 26 is opened, and the pressurizing pump 30 and the recycling pump 10 are driven for the purpose of cleaning the flow line.

Next, the flow line in the three-way valve 18 between the ports A and C is closed, and the flow line between the ports A and B is opened. The mobile phase becomes a supercritical fluid after it has passed the preheating coil 20, and is circulated in the loop. A state where the base line of the output of the detector 16 is stabilized indicates the fact that the state has become a steady state. In this state, the sample is injected into the column comprising a part of the loop by turning the internal flow line of the sample injector 12 after the sample has been loaded. As a result of this, the sample mixture is separated into each component in the column 14, and the resolution factor increases as the recycle time of the mobile phase through the loop increases. If the peak band broadening outside the column 14 is neglected, the effective length of the column 14 becomes equal to the value obtained by multiplying the length of the column 14 by the recycle time of the mobile phase.

In a case where unnecessary components are detected by the detector 16 after a proper separation has been performed, the flow line in the three-way valve 18 is turned to the back-pressure regulator 20 so as to waste the unnecessary components. During this discharge, since the mobile phase is supplied from a fluid supplying device to the inside of the loop for the purpose of maintaining the inlet pressure of the circulating pump 10 at the predetermined pressure of the pressurizing pump 30, the unnecessary components can be discharged without any reduction in the pressure of the inside of the loop below the critical pressure.

On the other hand, when the component to be separated and purified is detected by the detector 16, the flow line in the three-way valve 18 is turned to the recycling pump 10. Next, when the resolution factor of this component reaches a proper level, the three-way valve 20 is turned to the back-pressure regulator 20 for the purpose of fractionating only the desired component in the container 23.

In a case where the modifier solvent 34 is employed, the modifier solvent 34 is transferred by the pump 38 at a predetermined rate with respect to the discharge of the pressurizing pump 30.

It is well known that, in SFC, a high pressure drop causes density decrease along the column toward outlet, resulting in reducing the efficiency. Therefore, the obtainable plate number is not in proportion to the column length.

However, according to this first embodiment, an advantage can be obtained in that the pressure reduction in the column 14 can be reduced, and the effective length of the column can be lengthened, whereby a sufficient separation rate to perform fractionation can be obtained.

Furthermore, according to this first embodiment, the mobile phase is only consumed in a quantity necessary to fill the loop and a quantity discharged at the time of fractionating a necessary component or removing unnecessary components. Therefore, even if a relatively large diameter separating column is employed, the running cost can be kept low.

(2) Second embodiment

In the above-described first embodiment, since the pressurizing pump 30 is controlled so as to maintain the pressure constant, the flowrate can vary and the flowrate of the modifier supplying pump 38 is not maintained constant. Therefore, it is impossible for the mixture ratio between the liquefied gas 22 and the modifier solvent 34 to be made substantially constant, resulting into poor reproducibility of the peak retention times.

Figure 2:
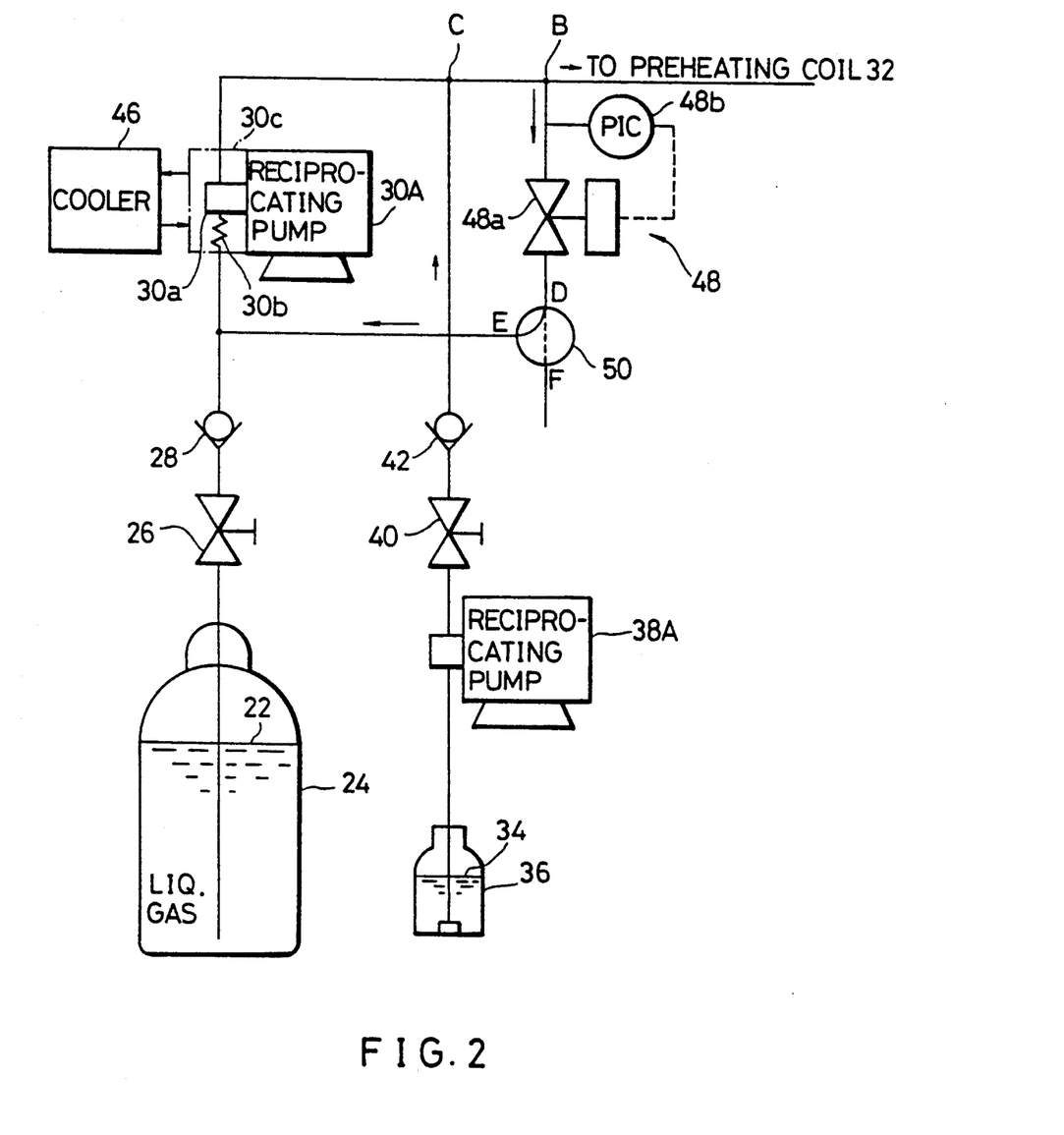
FIG. 2 shows the flow line of a mobile phase supplying device according to a second embodiment of the present invention.

In this second embodiment, a device shown in FIG. 2 is therefore used as the fluid supplying device in order to overcome the above-described problem.

That is, a reciprocating pump 30A is used as a pump for transferring the liquefied gas 22, the reciprocating pump 30A transferring a predetermined flow. In order to maintain the mobile phase in a pump head 30a of the reciprocating pump 30A to be fluid, a cooling coil 30b is connected to the inlet of the pump head 30a, the pump head 30a and the cooling coil 30b are covered with a cooling jacket 30c, and the inside of the cooling jacket 30c is maintained below a boiling point by a cooler 46. In general, cooling means of the type described above needs to be provided for the pressurizing pump 30 shown in FIG. 1.

Furthermore, as a pump for transferring the modifier solvent 34, a reciprocating pump 38A is employed which transfers it in a predetermined quantity in proportion to the predetermined discharge of the reciprocating pump 30A. These reciprocating pumps 30A and 38A generally comprise a plunger type pump.

The inlet of a back-pressure regulator 48 is connected to the point B to the lower stream of the intersecting point C between the liquefied gas 22 and the modifier solvent 34. The outlet of the back-pressure regulator 48 is connected to a port D of a three-way valve 50. A port E of the three-way valve 50 is connected to the flow line between the check valve 28 and the cooling coil 30b. The back-pressure regulator 48 comprises, similarly to the back-pressure regulator 20 shown in FIG. 1, a pressure regulating valve 48a and a pressure regulator 48b. Either the flow line between the ports D and E in the three-way valve 50 or that between the ports D and F in the same is selectively connected to each other so that the port F in the three-way valve 50 is connected to the atmosphere.

The other structure is the same as that shown in FIG. 1. The intersecting point C between the liquefied gas 22 and the modifier solvent 34 may be located on the flow line between the check valve 28 and the pump head 30a.

Next, an operation of this mobile phase supplying device will be described.

In a case where only the liquefied gas 22 is used as the mobile phase, the cooler 46 is driven for the purpose of cooling down the inside of the cooling jacket 30c below the critical temperature. Furthermore, the discharge of the reciprocating pump 30A is arranged to be a predetermined value which exceeds the maximum supply to the recycle portion, the pressure of the pressure regulator 48b is arranged to be a predetermined level which exceeds the critical pressure, and the flow line between the ports D and E in the three-way valve 50 is connected. Next, the shut-off valve 26 is opened to drive the reciprocating pump 30A.

The mobile phase supply pressure is maintained to the predetermined pressure of the back-pressure regulator 48 even if the ratio (split ratio) between the flow supplied to the back-pressure regulator 48 and the flow supply to the preheating coil 32 is changed. Furthermore, since a part of the mobile phase is fed back to the inlet of the reciprocating pump 30A, the mobile phase consumption can be kept low.

In a case where the liquefied gas 22 and the modifier solvent 34 are used as the mobile phase, the flow line between the ports D and F in the three-way valve 50 is connected to waste the mixed fluid. The reason for this lies in that a state where the mixing ratio between the liquefied gas 22 and the modifier solvent 34 must be constant. That is, when the ports D and F in the three-way valve 50 are connected to each other, in the state where no fluid is consumed in the recycling loop, the pump 30A takes in the same amount of the fluid discharged by itself whereas, the pump 38A always discharges new solvent. Therefore the modifier solvent accumulates in the loop comprising elements 48a, 50, 30b and 30a. Therefore, the excessive amount of the mixed fluid should be wasted and should not be fed back to the delivery system.

Next, the flow arranged for the reciprocating pump 38A is made constant with respect to a predetermined flow rate (which is constant) arranged for the reciprocating pump 30A, and the shut-off valve 40 is opened together with the shut-off valve 26.

In this case, even if the split ratio is changed, the supply pressure can be maintained at the predetermined pressure arranged for the pressure regulator 48b. Furthermore, an advantage can be obtained in that since the flowrate set for the reciprocating pumps 30A and 38A is constant and each split ratio for the liquefied gas 22 and the modifier solvent 34 becomes the same value, the mixing ratio between the liquefied gas 22 and the modifier solvent 34 can be maintained at the ratio between the flows of the reciprocating pumps 30A and 38A even if slight leakage from a seal for the reciprocating pump 10 and so forth is compensated in a steady state.

(3) Experiment

Experiment results using a device according to the above-described second embodiment will now be described.

Test Conditions

The pressure and the modifier concentration of the fluid delivered to the recycling flow line is always kept constant, even during a peak component is being collected in the following way. When the recycling mobile phase is consumed for peak collection, the mobile phase is automatically compensated by reducing the amount of fluid fed back to the pump 30A or wasted from the back-pressure regulator 48, maintaining the pressure constant in the recycling flow line. In order to reduce the fluid consumption, the flows of the pumps can be lowered during recycling is performed without collection.

SFC conditions were: column inlet pressure, 26.7 MPa; column outlet pressure, 25.0 MPa; control pressure of pumps (30A) and (38A), 25.0 MPa; recycling pump(10)flow, ca. 6 g/min; modifier solvent(34)flow, 0.15 ml/min.

Carbon dioxide was purchased from Tokyo Kagaku, Kawasaki, Japan, and was used as the mobile phase. Ethanol, HPLC grade was mixed with carbon dioxide as a modifier solvent.

A test mixture containing 1 mg each of di-n-and di-iso-butylphthalates was used for the testing the separation by recycle SFC. As a test solute for measuring the column efficiency, di-n-octylphthalate was used. All chemicals were purchased from Wako Pure Chemicals, Osaka, Japan, except for carbon dioxide.

A JASCO SuperMegaPak SIL column, 10 mm I.D.×250 mm length was used, the packing material was 5 μm silica gel.

Results

Separation of isomers of dibutylphthalate by recycle SFC

Figure 3A:
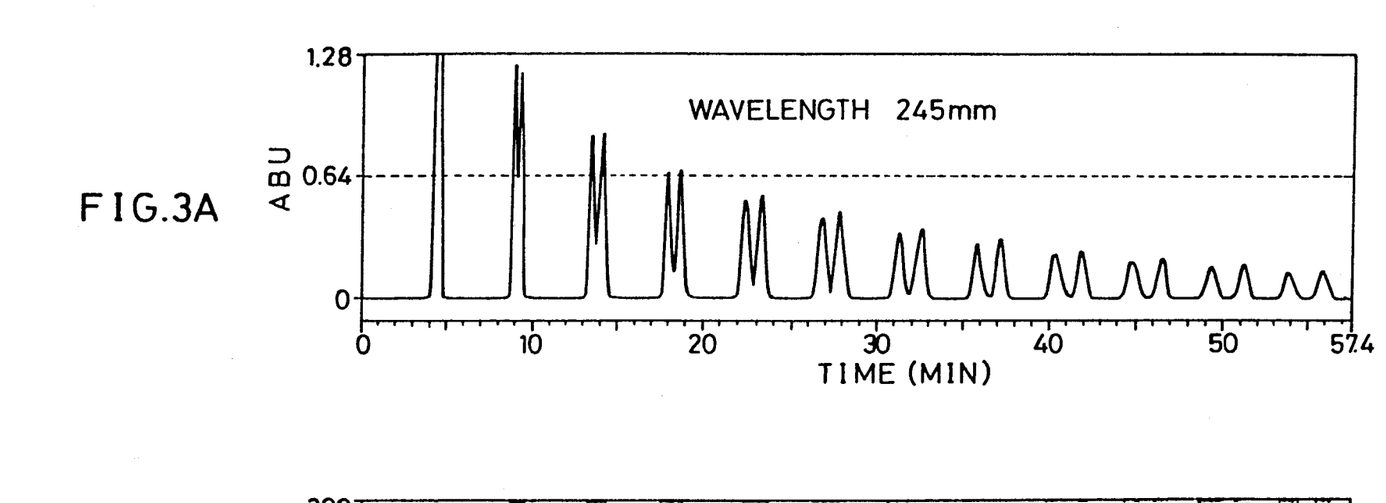
FIG. 3A shows a recycle chromatogram when the wavelength is 245 nm.

FIG. 3A shows the recycle chromatogram.

Figure 3B:
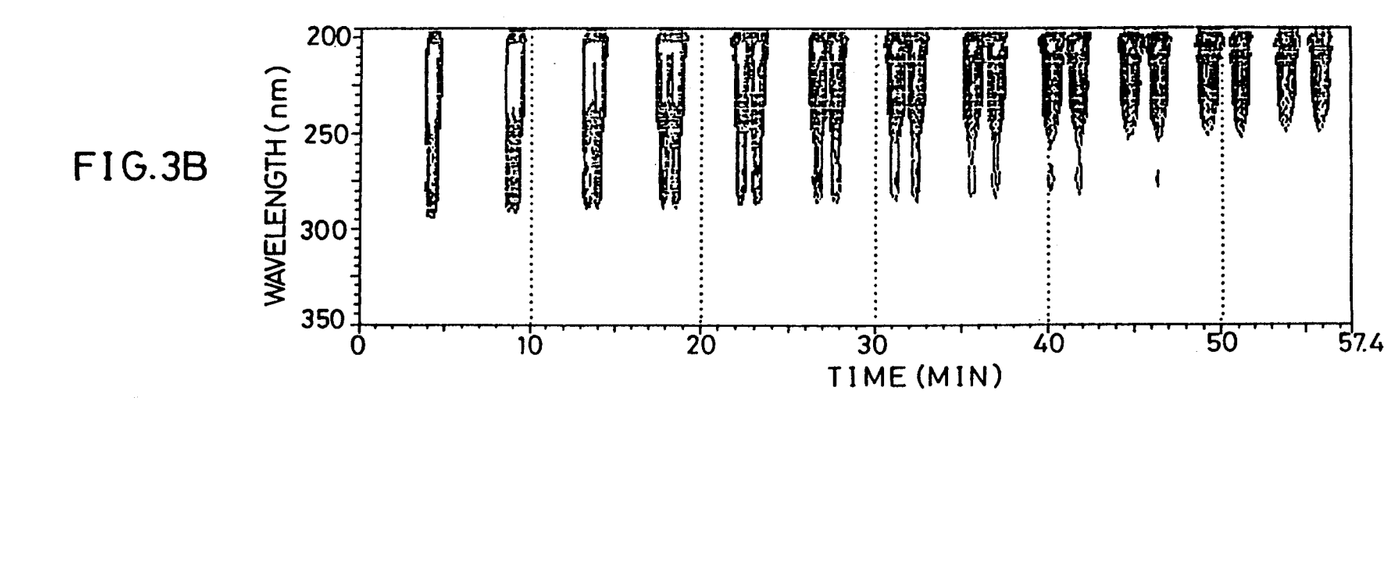
FIG. 3B is a contour plot of the above chromatogram.

As shown, the recycle operation has been performed successfully and symmetric peaks are obtained even after twelve time recycling, and the resolution increases with the number of recycles. The contour plot shown in FIG. 3B dramatically indicates that the above two compounds are completely separated to base line after ten time recycling, while the first peak without recycling shows very poor separation and looks almost like a fused peak. Efficiency with respect to the number of recycles Di-n-octylphthalate, which gave a capacity factor of ca. 1 under the same conditions as given above, was subjected to recycle SFC for calculating the column efficiency.

Figure 4:
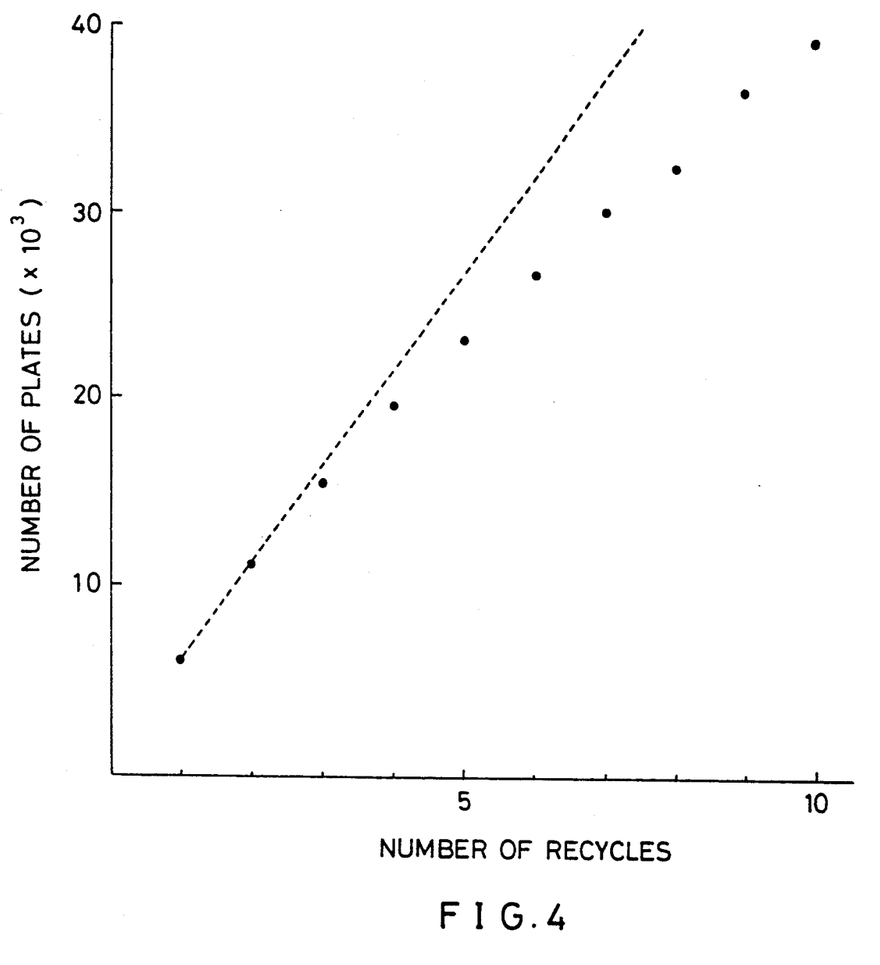
FIG. 4 shows the relationship between the number of recycles and the number of plates.

The relationship between the number of recycles and the number of plates N is shown in FIG. 4. A plate number was calculated by using the peak area and height, assuming that the concentration distribution is Gaussian.

It is remarkable that $39.2 \times 10^3$ plates have been obtained with a column pressure drop $\Delta P$ of only 1.7 MPa after ten time recycling, whereas the first cycle or elution without recycling offered only $6.1 \times 10^3$ plates with the same pressure drop.

The relationship is not linear, but was in convex shape as shown in the figure. This means, assuming that variance additivity be held, that there is some effect which makes the peak width wider as the solute resident time in the system becomes longer, besides the extracolumn band broadening caused by instrumental variance, preventing the plate number from increasing in proportion to the number of recycles. This extra broadening might be attributed to a high molecular diffusivity in supercritical carbon dioxide and too slow a linear velocity.

This new method has a potential capability that opens up a new phase in the application of supercritical fluid to preparative separation.

(4) Third Embodiment

Figure 5:
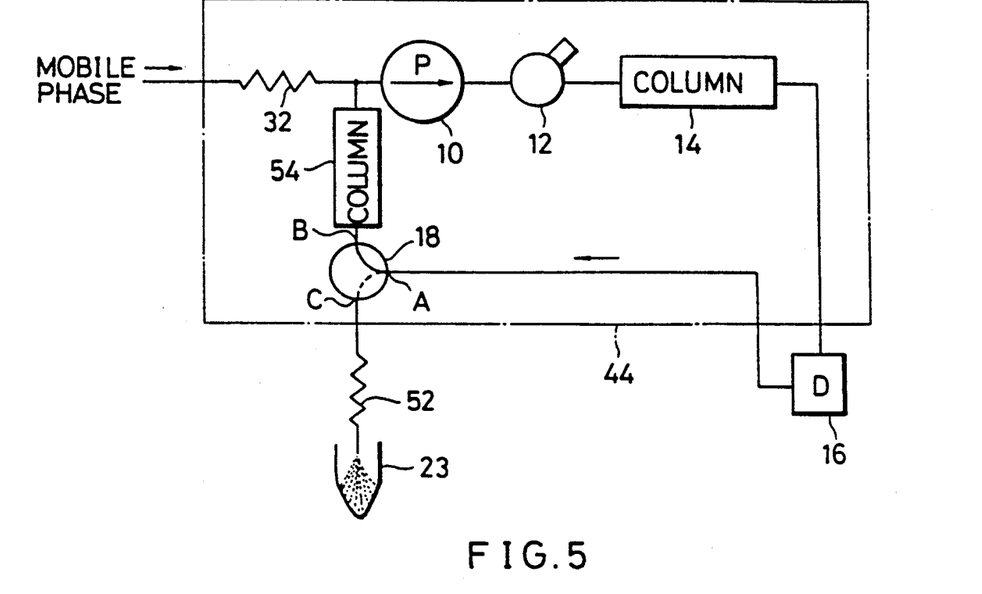
FIG. 5 shows a flow line for a recycle portion according to a third embodiment.

FIG. 5 shows a recycle portion of a third embodiment.

In this third embodiment, its structure can be formed simply since a resistance pipe 52 is employed as an alternative to the back-pressure regulator 20 shown in FIG. 1.

Furthermore, since a column 54 is interposed in a flow line between the port B of the three-way valve 18 and the inlet of the recycling pump 10, an advantage can be obtained in that a necessary component can be retained for a while in the column 54 without discharging it, and unnecessary components succeeding the necessary component can be discharged. That is, since the fluid does not pass through the column 54 during this discharge, a necessary component can be retained in the column 54 without discharging it.

This column 54 may, of course, be provided for the structure shown in FIG. 1.

(5) Fourth Embodiment

Figure 6:
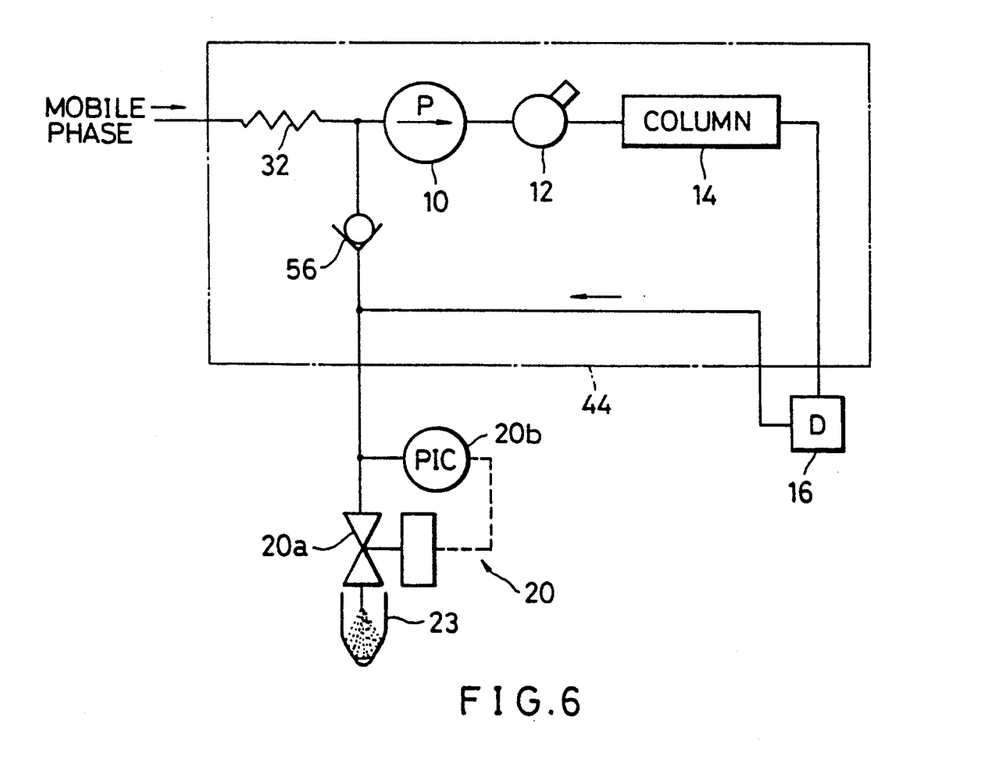
FIG. 6 shows a flow line for a recycle portion according to a fourth embodiment.

FIG. 6 shows a recycle portion according to a fourth embodiment.

In this fourth embodiment, a check valve 56 is used as an alternative to the three-way valve 18 shown in FIG. 1 so that the mobile phase is prevented from passing from the preheating coil 32 to the back-pressure regulator 20 during removal of unnecessary components or during fractionating a necessary component. Furthermore, the back-pressure regulator 20 is connected to a flow line between the outlet of the detector 16 and the inlet of the check valve 56. This pressure regulating valve 20 is completely closed during recycle. This check valve 56 does not necessarily need to be provided.

In each of the above-described embodiments, the separation conditions may be, as need, changed by changing the pressure and the temperature of the supercritical fluid in accordance with the output of the detector 16 or the time elapse.

What is claimed is:

1. A recycle chromatograph with supercritical fluid as a mobile phase comprising:
    a recycling pump (10) for transferring a mobile phase at a predetermined flow rate;

a sample injector (12) having an inlet connected to an outlet of said recycling pump via a flow line;

a first column (14) having an inlet connected to an outlet of said sample injector via a flow line, said first column being filled with a stationary phase;

a detector (16) having an inlet connected to an outlet of said column via a flow line, said detector detecting the components of a sample;

flow line switching means (18) having an inlet connected to an outlet of said detector via a flow line, while one of two outlets of said flow line switching means is connected to said recycling pump via a flow line, said two outlets being selectively connected to said inlet thereof;

a first back-pressure regulator (20) having an inlet connected to another of said flow line switching means via a flow line, an outlet of which is connected to the atmosphere;

pressurizing pump means (30) connected to a flow line between said one of said two outlets of said flow line switching means and an inlet of said recycling pump via a flow line, said pressurizing pump means supplying a mobile phase to said recycling pump so that supplied mobile phase pressure becomes a predetermined pressure;

a first pump (30A) for transferring a liquefied gas to a predetermined flowrate; and a second back-pressure regulator (48) connected to the outlet flow line of said first pump via a flow line, said second back-pressure regulator maintaining the back pressure at a predetermined level.

2. A recycle chromatograph with supercritical fluid as mobile phase according to claim 1, wherein said mobile phase supplying means further comprises:

a second pump (38A) the outlet of which is connected to a flow line between an intersecting point of the outlet flow line of said first pump and the inlet flow line of said second back-pressure regulator and the outlet of said first pump via a flow line, said second pump transferring modifier solvent by a predetermined flowrate.

3. A recycle chromatograph with supercritical fluid as mobile phase according to claim 2, further comprising:

flow line switching means (50) having an inlet connected to the outlet of said second back-pressure regulator via a flow line, while either of the two outlets of said flow line switching means is connected to the inlet of said first pump, said two outlets being selectively connected to said inlet thereof, while another outlet is connected to the atmosphere.

4. A recycle chromatograph with supercritical fluid as mobile phase according to claim 1, wherein said second pump has an outlet connected to the inlet flow line of said first pump; said second pump transferring modifier solvent by a predetermined flowrate.

* * * * *